United States Patent [19]

Annen et al.

[11] 4,435,390
[45] Mar. 6, 1984

[54] HYDROCORTISONE DERIVATIVES, THE PREPARATION AND USE THEREOF

[75] Inventors: Klaus Annen; Henry Laurent; Helmut Hofmeister; Rudolf Wiechert, all of Berlin, Fed. Rep. of Germany

[73] Assignee: Schering Aktiengesellschaft, Berlin and Bergkamen, Fed. Rep. of Germany

[21] Appl. No.: 409,263

[22] Filed: Aug. 18, 1982

[30] Foreign Application Priority Data

Aug. 18, 1981 [DE] Fed. Rep. of Germany ....... 3133082

[51] Int. Cl.³ .......................... C07J 5/00; A61K 31/56
[52] U.S. Cl. ................................ 424/243; 260/397.45
[58] Field of Search ..................................... 260/397.45

[56] References Cited

U.S. PATENT DOCUMENTS

| 2,897,218 | 7/1959 | Sebek et al. | 260/397.45 |
| 3,053,832 | 9/1962 | Gould | 260/397.45 |
| 3,891,631 | 6/1975 | Phillipps et al. | 260/397.45 |
| 4,290,962 | 9/1981 | Tachi et al. | 260/397.45 |

OTHER PUBLICATIONS

J. Amer. Chem. Soc., 78, 1956, 6213.
J. Amer. Chem. Soc., 81, 1959, 1235.

Primary Examiner—Elbert L. Roberts
Attorney, Agent, or Firm—Millen & White

[57] ABSTRACT

Hydrocortisone derivatives of Formula I

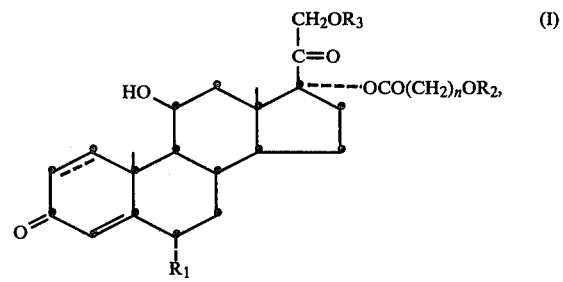

wherein
═ is a single bond or a double bond,
n is 1 or 2,
$R_1$ is hydrogen or methyl,
$R_2$ is alkyl of 1–6 carbon atoms, and
$R_3$ is hydrogen or 1-oxoalkyl (alkanoyl) of 2–6 carbon atoms, are pharmacologically active compounds, e.g., as antiinflammatories.

27 Claims, No Drawings

HYDROCORTISONE DERIVATIVES, THE PREPARATION AND USE THEREOF

The present invention concerns new hydrocortisone derivatives.

SUMMARY OF THE INVENTION

It is an object of this invention to provide new hydrocortisone derivatives having valuable pharmacological properties.

Upon further study of the specification and appended claims, further objects and advantages of this invention will become apparent to those skilled in the art.

These objects have been achieved by providing hydrocortisone derivatives of Formula I

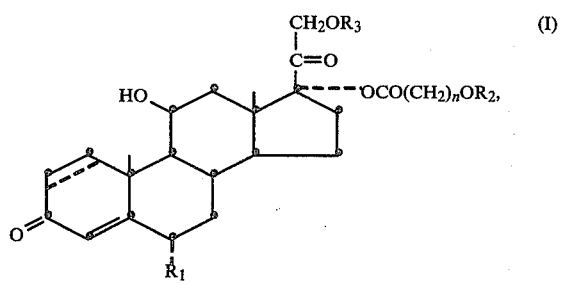

wherein

----- is a single bond or a double bond,
n is 1 or 2,
$R_1$ is hydrogen or methyl,
$R_2$ is alkyl of 1-6 carbon atoms, and
$R_3$ is hydrogen or 1-oxoalkyl (alkanoyl) of 2-6 carbon atoms.

DETAILED DISCUSSION

The novel hydrocortisone derivatives of Formula I can carry, as the 1-oxoalkyl (alkanoyl) groups $R_3$ of 2-6 carbon atoms, for example, acetyl, propionyl, butyryl, isobutyryl, valeryl, 3-methyl-butyryl, trimethylacetyl, hexanoyl, etc.

The hydrocortisone derivatives of Formula I can carry, as the alkyl group $R_2$, for example, methyl, ethyl, propyl, isopropyl, butyl, sec-butyl, tert-butyl, pentyl, etc.

The derivatives of hydrocortisone of this invention exhibit a strong antiinflammatory activity upon topical administration. Upon systemic administration, these hydrocortisone derivatives are of a relatively weak activity, making them very desirable as topical agents.

The novel hydrocortisone derivatives of Formula I are, accordingly, suitable, in combination with the excipients customary in galenic pharmacy, for the local treatment of contact dermatitis, eczemas of a great variety of types, neurodermatoses, erythrodermia, burns, pruritus vulvae et ani, rosacea, erythematodes cutaneus, psoriasis, lichen ruber planus et verrucosus, and similar skin disorders.

The drug specialties can be prepared as usual by converting the active agents with suitable additives into the desired form of administration, such as for example: solutions, lotions, ointments, creams, or plasters. In the thus-formulated medicines, the active agent concentration is dependent on the form of administration. In the case of lotions and ointments, an active agent concentration of 0.001-1% is preferably employed.

Moreover, the novel compounds, optionally in combination with the usual excipients and auxiliary agents, are also well suited for the preparation of inhalants usable for the therapy of allergic diseases of the respiratory tract, e.g. bronchial asthma or rhinitis.

The novel corticoids are furthermore suitable, in the form of capsules, tablets, or dragees containing preferably 10-200 mg of active agent and administered orally or in the form of suspensions, preferably containing 100-500 mg of active agent per dosage unit and administered rectally, also for the treatment of allergic diseases of the intestinal tract, such as colitis ulcerosa and colitis granulomatosa.

For all of these uses, the administration of the compounds of this invention, e.g., to mammals, including humans, is analogous to that of known hydrocortisone type agents such as hydrocortisone-27-butyrate, for treatment of inflammation.

The pharmacologically active compounds of this invention can be processed in accordance with conventional methods of galenic pharmacy to produce medicinal agents for administration to patients, e.g., mammals including humans. Conventional excipients are pharmaceutically acceptable organic or inorganic carrier substances suitable for topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For topical application, the compounds can be employed as non-sprayable forms, viscous to semi-solid or solid forms comprising a carrier indigenous to topical application and having a dynamic viscosity preferably greater than water. Suitable formulations include but are not limited to solutions, suspensions, lotions, emulsions, creams, ointments, plasters, powders, linaments, salves, aerosols, etc. For topical application, also suitable are sprayable aerosol preparations wherein the active ingredient, preferably in combination with a solid or liquid inert carrier material, is packaged in a squeeze bottle or in admixture with a pressurized volatile, normally gaseous propellant, e.g., a freon.

In the thus-formulated medicinal agents, the effective agent concentration is dependent on the compound used and the form of application and can be easily determined by clinical tests under conventional considerations. Usually, the active compounds of the invention are incorporated in topical formulations in a preferred concentration of about 0.001 to 1 wt. %.

The method and repetition of administration will vary with the particular form of administration and the indication involved, but will normally be from 1 to 10 times daily.

The novel hydrocortisone derivatives can be prepared according to the conventional methods which can be performed under known conditions, e.g., those described in German Patent Applications Nos.

2,645,104; 2,645,105; and 2,340,591, whose disclosures are incorporated by reference herein. These processes include rearranging a hydrocortisone 21-acylate of Formula II

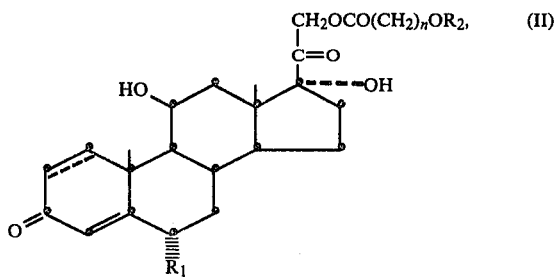

wherein $\overline{\overline{\phantom{==}}}$, $R_1$, and $R_2$ are as defined above, to the corresponding 17-acrylate; optionally esterifying the product in the 21-position; and, if desired, hydrogenating the $\Delta^{1,4}$-steroids of Formula I to the $\Delta^4$-steroids.

All starting materials are known or conventionally preparable by conventional methods using known or available materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(a) At 0° C., 15.0 g of 11β,17,21-trihydroxy-4-pregnene-3,20-dione in 150 ml of pyridine is agitated with 9 ml of methoxyacetic acid chloride for 3 hours. The mixture is then poured on an ice water-sodium chloride solution, the precipitate is filtered off and purified on 1.1 kg of silica gel with a methylene chloride-acetone gradient (0–20% acetone). Yield: 15.2 g of 11β,17-dihydroxy-21-methoxyacetoxy-4-pregnene-3,20-dione, mp 232° C.

(b) At 0° C. under argon, 20 ml of a 5% solution of methyllithium in ether is added dropwise to a suspension of 3.2 g of copper(I) iodide in 64 ml of anhydrous tetrahydrofuran. The yellow solution is cooled to −30° C., and a solution of 2.9 g of 11β,17-dihydroxy-21-methoxyacetoxy-4-pregnene-3,20-dione in 100 ml of anhydrous tetrahydrofuran is added thereto. The mixture is further stirred for 20 minutes at −30° C. and poured on an aqueous ammonium chloride solution. After extraction with methylene chloride, the organic solution is washed, dried over sodium sulfate, and evaporated under vacuum. The crude product is purified on 220 g of silica gel with a methylene chloride-acetone gradient (0–25% acetone), thus isolating 1.4 g of 11β,21-dihydroxy-17-methoxyacetoxy-4-pregnene-3,20-dione, mp 185° C.

EXAMPLE 2

(a) Analogously to Example 1(a), 10.0 g of 11β,17,21-trihydroxy-4-pregnene-3,20-dione in 100 ml of pyridine is reacted with 6 ml of ethoxyacetic acid chloride, worked up, and purified. Yield: 10.3 g of 21-ethoxyacetoxy-11β,17-dihydroxy-4-pregnene-3,20-dione, mp 203° C.

(b) Under the conditions of Example 1(b), 10.0 g of 21-ethoxyacetoxy-11β,17-dihydroxy-4-pregnene-3,20-dione is rearranged with lithium dimethyl cuprate and worked up. The crude product is purified on 700 g of silica gel with a hexane-ethyl acetate gradient (0–100% ethyl acetate), thus obtaining 4.1 g of 17-ethoxyacetoxy-11β,21-dihydroxy-4-pregnene-3,20-dione, mp 161° C.

EXAMPLE 3

(a) As described in Example 1(a), 20.0 g of 11β,17,21-trihydroxy-4-pregnene-3,20-dione in 200 ml of pyridine is reacted with 3-methoxypropionic acid chloride, worked up, and purified. Yield: 12.8 g of 11β,17-dihydroxy-21-(3-methoxypropionyloxy)-4-pregnene-3,20-dione, mp 188° C.

(b) Analogously to Example 1(b), 11.5 g of 11β,17-dihydroxy-21-(3-methoxypropionyloxy)-4-pregnene-3,20-dione is rearranged with lithium dimethyl cuprate and worked up. Purification on 750 g of silica gel with a methylene chloride-acetone gradient (0–30% acetone) yields 7.3 g of 11β,21-dihydroxy-17-(3-methoxypropionyloxy)-4-pregnene-3,20-dione, mp 172° C.

EXAMPLE 4

(a) Under the conditions of Example 1(a), 10.0 g of 11β,17,21-trihydroxy-4-pregnene-3,20-dione is reacted with 3-ethoxypropionic acid chloride and chromatographed on 1.5 kg of silica gel with a hexane-ethyl acetate gradient (0–70% ethyl acetate). Yield: 9.7 g of 21-(3-ethoxypropionyloxy)-11β,17-dihydroxy-4-pregnene-3,20-dione, mp 126° C.

(b) 9.0 g of 21-(3-ethoxypropionyloxy)-11β,17-dihydroxy-4-pregnene-3,20-dione is rearranged with lithium dimethyl cuprate, as described in Example 1(b), worked up, and chromatographed, thus isolating 3.1 g of 17-(3-ethoxypropionyloxy)-11β,21-dihydroxy-4-pregnene-3,20-dione, mp 149° C.

EXAMPLE 5

(a) A solution of 10.0 g of 11β,17,21-trihydroxy-1,4-pregnadiene-3,20-dione in pyridine is reacted analogously to Example 1(a) with methoxyacetic acid chloride, worked up, and purified, thus isolating 10.3 g of 11β,17-dihydroxy-21-methoxyacetoxy-1,4-pregnadiene-3,20-dione.

(b) 9.0 g of 11β,17-dihydroxy-21-methoxyacetoxy-1,4-pregnadiene-3,20-dione is rearranged analogously to Example 1(b) with lithium dimethyl cuprate, worked up, and purified. Yield: 3.6 g of 11β,21-dihydroxy-17-methoxyacetoxy-1,4-pregnadiene-3,20-dione.

(c) 1.5 g of 11β,21-dihydroxy-17-methoxyacetoxy-1,4-pregnadiene-3,20-dione is stirred in 15 ml of pyridine and 7.5 ml of acetic anhydride for 2 hours at room temperature. The mixture is then poured on an ice water-sodium chloride solution, the precipitate is filtered off, and the crude product is purified on 100 g of silica gel with a methylene chloride-acetone gradient (0–20% acetone). Yield: 1.2 g of 21-acetoxy-11β-hydroxy-17-methoxyacetoxy-1,4-pregnadiene-3,20-dione.

EXAMPLE 6

(a) 10.0 g of 11β,17,21-trihydroxy-1,4-pregnadiene-3,20-dione is reacted analogously to Example 2(a) with ethoxyacetic acid chloride, worked up, and purified, thus isolating 10.4 g of 21-ethoxyacetoxy-11β,17-dihydroxy-1,4-pregnadiene-3,20-dione.

(b) Analogously to Example 2(b), 6.0 g of 21-ethoxyacetoxy-11β,17-dihydroxy-1,4-pregnadiene-3,20-dione is rearranged with lithium dimethyl cuprate, worked up, and purified, yielding 2.5 g of 17-ethoxyacetoxy-11β,21-dihydroxy-1,4-pregnadiene-3,20-dione.

EXAMPLE 7

(a) Under the conditions of Example 3(a), 10.0 g of 11β,17,21-trihydroxy-1,4-pregnadiene-3,20-dione is reacted with 3-methoxypropionic acid chloride, worked up, and purified, thus isolating 7.3 g of 11β,17-dihydroxy-21-(3-methoxypropionyloxy)-1,4-pregnadiene-3,20-dione.

(b) Analogously to Example 1(b), 7.0 g of 11β,17-dihydroxy-21-(3-methoxypropionyloxy)-1,4-pregnadiene-3,20-dione is rearranged with lithium dimethyl cuprate, worked up, and purified. Yield: 3.9 g of 11β,21-dihydroxy-17-(3-methoxypropionyloxy)-1,4-pregnadiene-3,20-dione.

(c) As described in Example 5(c), 1.0 g of 11β,21-dihydroxy-17-(3-methoxypropionyloxy)-1,4-pregnadiene-3,20-dione is reacted with acetic anhydride at room temperature, worked up, and purified, thus isolating 810 mg of 21-acetoxy-11β-hydroxy-17-(3-methoxypropionyloxy)-1,4-pregnadiene-3,20-dione.

EXAMPLE 8

(a) 15.0 g of 11β,17,21-trihydroxy-6α-methyl-1,4-pregnadiene-3,20-dione is reacted analogously to Example 1(a) with methoxyacetic acid chloride, worked up, and purified. Yield: 15.4 g of 11β,17-dihydroxy-21-methoxyacetoxy-6α-methyl-1,4-pregnadiene-3,20-dione, mp 219° C.

(b) Under the conditions of Example 1(b), 15.0 g of 11β,17-dihydroxy-21-methoxyacetoxy-6α-methyl-1,4-pregnadiene-3,20-dione is rearranged with lithium dimethyl cuprate and worked up. The crude product is purified on 400 g of silica gel with a hexane-acetone gradient (0–50% acetone). Yield: 9.3 g of 11β,21-dihydroxy-17-methoxyacetoxy-6α-methyl-1,4-pregnadiene-3,20-dione, mp 202° C.

EXAMPLE 9

2.0 g of 11β,21-dihydroxy-17-methoxyacetoxy-6α-methyl-1,4-pregnadiene-3,20-dione is reacted under the conditions of Example 5(c) with acetic anhydride, worked up, and purified. Yield: 1.6 g of 21-acetoxy-11β-hydroxy-17-methoxyacetoxy-6α-methyl-1,4-pregnadiene-3,20-dione, mp 151° C.

EXAMPLE 10

(a) As described in Example 2(a), 15.0 g of 11β,17,21-trihydroxy-6α-methyl-1,4-pregnadiene-3,20-dione is reacted with ethoxyacetic acid chloride, worked up, and purified, thus isolating 15.6 g of 21-ethoxyacetoxy-11β,17-dihydroxy-6α-methyl-1,4-pregnadiene-3,20-dione, mp 229° C.

(b) 15.0 g of 21-ethoxycaetoxy-11β,17-dihydroxy-6α-methyl-1,4-pregnadiene-3,20-dione is rearranged with lithium dimethyl cuprate under the conditions of Example 2(b), worked up, and purified. Yield: 8.3 g of 17-ethoxyacetoxy-11β,21-dihydroxy-6α-methyl-1,4-pregnadiene-3,20-dione, mp 198° C.

EXAMPLE 11

2.0 g of 17-ethoxyacetoxy-11β,21-dihydroxy-6α-methyl-1,4-pregnadiene-3,20-dione is reacted analogously to Example 5(c) with acetic anhydride, worked up, and purified. Yield: 1.9 g of 21-acetoxy-17-ethoxyacetoxy-11β-hydroxy-6α-methyl-1,4-pregnadiene-3,20-dione, mp 170° C.

EXAMPLE 12

(a) Under the conditions of Example 3(a), 15.0 g of 11β,17,21-trihydroxy-6α-methyl-1,4-pregnadiene-3,20-dione is reacted with 3-methoxypropionic acid chloride, worked up, and purified, thus isolating 14.3 g of 11β,17-dihydroxy-6α-methyl-21-(3-methoxypropionyloxy)-1,4-pregnadiene-3,20-dione, mp 230° C.

(b) 8.8 g of 11β,17-dihydroxy-21-6α-methyl-21-(3-methoxypropionyloxy)-1,4-pregnadiene-3,20-dione is rearranged with lithium dimethyl cuprate analogously to Example 3(b), worked up, and purified. Yield: 3.2 g of 11β,21-dihydroxy-17-(3-methoxypropionyloxy)-6α-methyl-1,4-pregnadiene-3,20-dione, mp 151° C.

EXAMPLE 13

2.0 g of 11β,21-dihydroxy-17-(3-methoxypropionyloxy)-6α-methyl-1,4-pregnadiene-3,20-dione is reacted analogously to Example 5(c) with acetic anhydride, worked up, and purified, thus isolating 1.36 g of 21-acetoxy-11β-hydroxy-17-(3-methoxypropionyloxy)-6α-methyl-1,4-pregnadiene-3,20-dione, mp 162° C.

EXAMPLE 14

(a) 15.0 g of 11β,17,21-trihydroxy-6α-methyl-1,4-pregnadiene-3,20-dione is reacted analogously to Example 4(a) with 3-ethoxypropionic acid chloride, worked up, and purified, thus isolating 13.6 g of 21-(3-ethoxypropionyloxy)-11β,17-dihydroxy-6α-methyl-1,4-pregnadiene-3,20-dione, mp 186° C.

(b) The rearrangement of 10.0 g of 21-(3-ethoxypropionyloxy)-11β,17-dihydroxy-6α-methyl-1,4pregnadiene-3,20-dione with lithium dimethyl cuprate is conducted analogously to Example 4(b). After working up to the reaction mixture and purification, 4.1 g of 17-(3-ethoxypropionyloxy)-11β,21-dihydroxy-6α-methyl-1,4-pregnadiene-3,20-dione is obtained, mp 167° C.

EXAMPLE 15

As described in Example 5(c), 2.0 g of 17-(3-ethoxypropionyloxy)-11β,21-dihydroxy-6α-methyl-1,4-pregnadiene-3,20-dione is reacted with acetic anhydride, worked up, and purified. Yield: 1.34 g of 21-acetoxy-17-(3-ethoxypropionyloxy)-11β-hydroxy-6α-methyl-1,4-pregnadiene-3,20-dione, mp 131° C.

EXAMPLE 16

Analogously to Example 5(c), 1.0 g of 11β,21-dihydroxy-17-methoxyacetoxy-6α-methyl-1,4-pregnadiene-3,20-dione is reacted at room temperature with propionic anhydride, worked up, and purified, thus isolating 780 mg of 11β-hydroxy-17-methoxyacetoxy-21-propionyloxy-6α-methyl-1,4-pregnadiene-3,20-dione.

EXAMPLE 17

Under the conditions of Example 5(c), 1.2 g of 11β,21-dihydroxy-17-methoxyacetoxy-6α-methyl-1,4-pregnadiene-3,20-dione is reacted at room temperature with butyric anhydride, worked up, and purified, thus obtaining 730 mg of 21-butyryloxy-11β-hydroxy-17-methoxyacetoxy-6α-methyl-1,4-pregnadiene-3,20-dione.

EXAMPLE 18

1.0 g of 11β,21-dihydroxy-17-methoxyacetoxy-6α-methyl-1,4-pregnadiene-3,20-dione is reacted under the conditions of Example 5(c) with isobutyric anhydride, worked up, and purified, yielding 590 mg of 11β-hydroxy-21-isobutyryloxy-17-methoxyacetoxy-6α-methyl-1,4-pregnadiene-3,20-dione.

EXAMPLE 19

3.0 g of 11β,21-dihydroxy-17-methoxyacetoxy-6α-methyl-1,4-pregnadiene-3,20-dione is hydrogenated in a mixture of 225 ml of benzene and 75 ml of methanol with 2.7 g of tris(triphenylphosphine)rhodium(I) chloride for 6.5 hours at room temperature. The reaction mixture is evaporated to dryness under vacuum, and the crude product is purified on 350 g of silica gel with a hexane-acetone gradient (0–50% acetone). Yield: 2.5 g of 11β,21-dihydroxy-17-methoxyacetoxy-6α-methyl-4-pregnene-3,20-dione.

EXAMPLE 20

Analogously to Example 19, 1.5 g of 21-acetoxy-11β-hydroxy-17-methoxyacetoxy-6α-methyl-1,4-pregnadiene-3,20-dione is hydrogenated with 1.2 g of tris(triphenylphosphine)rhodium(I) chloride, worked up, and purified. Yield: 1.1 g of 21-acetoxy-11β-hydroxy-17-methoxyacetoxy-6α-methyl-4-pregnene-3,20-dione.

EXAMPLE 21

1.0 g of 17-ethoxyacetoxy-11β,21-dihydroxy-6α-methyl-1,4-pregnadiene-3,20-dione is hydrogenated as described in Example 19 with 700 mg of tris(triphenylphosphine)rhodium(I) chloride. After the reaction mixture has been worked up and purified, 790 mg of 17-ethoxyacetoxy-11β,21-dihydroxy-6α-methyl-4-pregnene-3,20-dione is isolated.

EXAMPLE 22

Under the conditions of Example 19, 1.5 g of 21-acetoxy-11β-hydroxy-17-(3-methoxypropionyloxy)-6α-methyl-1,4-pregnadiene-3,20-dione is hydrogenated with 1.2 g of tris(triphenylphosphine)rhodium(I) chloride, worked up, and purified. Yield: 1.2 g of 21-acetoxy-11β-hydroxy-17-(3-methoxypropionyloxy)-6α-methyl-4-pregnene-3,20-dione.

EXAMPLE 23

(a) 1.5 g of 11β,17,21-trihydroxy-6α-methyl-4-pregnene-3,20-dione is reacted analogously to Example 1(a) with methoxyacetic acid chloride, worked up, and chromatographed, thus isolating 1.6 g of 11β,17-dihydroxy-21-methoxyacetoxy-6α-methyl-4-pregnene-3,20-dione.

(b) 1.5 g of 11β,17-dihydroxy-21-methoxyacetoxy-6α-methyl-4-pregnene-3,20-dione is rearranged uner the conditions of Example 1(b) with lithium dimethyl cuprate, worked up, and purified. Yield: 690 mg of 11β,21-dihydroxy-17-methoxyacetoxy-6α-methyl-4-pregnene-3,20-dione.

EXAMPLE 24

As described in Example 5(c), 600 mg of 11β,21-dihydroxy-17methoxyacetoxy-6α-methyl-4-pregnene-3,20-dione is reacted with acetic anhydride, worked up, and chromatographed, thus isolating 480 mg of 21-acetoxy-11β-hydroxy-17-methoxyacetoxy-6α-methyl-4pregnene-3,20-dione.

The preceding examples can be repeated with similar success by substituting the generically or specifically described reactants and/or operating conditions of this invention for those used in the preceding examples. From the foregoing description, one skilled in the art can easily ascertain the essential characteristics of this invention, and without departing from the spirit and scope thereof, can make various changes and modifications of the invention to adapt it to various usages and conditions.

What is claimed is:

1. A hydrocortisone derivative of the formula

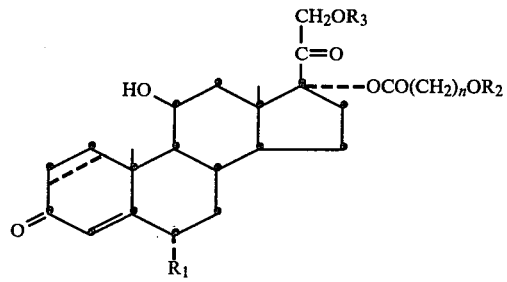

wherein

--- is a single bond or a double bond,
n is 1 or 2,
$R_1$ is hydrogen or methyl,
$R_2$ is alkyl of 1–6 carbon atoms, and
$R_3$ is hydrogen or alkanoyl of 2–6 carbon atoms.

2. 17-Ethoxyacetoxy-11β,21-dihydroxy-4-pregnene-3,20-dione, a compound of claim 1.

3. 11β,21-Dihydroxy-17-methoxyacetoxy-4-pregnene-3,20-dione, a compound of claim 1.

4. 17-(3-Ethoxypropionyloxy)-11β,21-dihydroxy-4-pregnene-3,20-dione, a compound of claim 1.

5. 11β,21-Dihydroxy-17-(3-methoxypropionyloxy)-4-pregnene-3,20-dione, a compound of claim 1.

6. 17-Ethoxyacetoxy-11β,21-dihydroxy-1,4-pregnadiene-3,20-dione, a compound of claim 1.

7. 21-Acetoxy-11β-hydroxy-17-(3-methoxypropionyloxy)-1,4-pregnadiene-3,20-dione, a compound of claim 1.

8. 11β,21-Dihydroxy-17-(3-methoxypropionyloxy)-6α-methyl-1,4-pregnadiene-3,20-dione, a compound of claim 1.

9. 21-Acetoxy-11β-hydroxy-17-(3-methoxypropionyloxy)-6α-methyl-1,4-pregnadiene-3,20-dione, a compound of claim 1.

10. 21-Acetoxy-11β-hydroxy-17-methoxyacetoxy-1,4-pregnadiene-3,20-dione, a compound of claim 1.

11. 17-Ethoxyacetoxy-11β,21-dihydroxy-6α-methyl-1,4-pregnadiene-3,20-dione, a compound of claim 1.

12. 17-(3-Ethoxypropionyloxy)-11β,21-dihydroxy-6α-methyl-1,4-pregnadiene-3,20-dione, a compound of claim 1.

13. 21-Acetoxy-17-(3-ethoxypropionyloxy)-11β-hydroxy-6α-methyl-1,4-pregnadiene-3,20-dione, a compound of claim 1.

14. 11β-Hydroxy-17-methoxyacetoxy-21-propionyloxy-6α-methyl-1,4pregnadiene-3,20-dione, a compound of claim 1.

15. 21-Butyryloxy-11β-hydroxy-17-methoxyacetoxy-6α-methyl-1,4-pregnadiene-3,20-dione, a compound of claim 1.

16. 21-Acetoxy-11β-hydroxy-17-methoxyacetoxy-6α-methyl-1,4-pregnadiene-3,20-dione, a compound of claim 1.

17. 11β-Hydroxy-21-isobutyryloxy-17-methoxyacetoxy-6α-methyl-1,4-pregnadiene-3,20-dione, a compound of claim 1.

18. 21-Acetoxy-17-ethoxyacetoxy-11β-hydroxy-6α-methyl-1,4-pregnadiene-3,20-dione, a compound of claim 1.

19. 11β,21-Dihydroxy-17-methoxyacetoxy-6α-methyl-4-pregnene-3,20-dione, a compound of claim 1.

20. 17-Ethoxyacetoxy-11β,21-dihydroxy-6α-methyl-4-pregnene-3,20-dione, a compound of claim 1.

21. 21-Acetoxy-11β-hydroxy-17-methoxyacetoxy-6α-methyl-4-pregnene-3,20-dione, a compound of claim 1.

22. 21-Acetoxy-11β-hydroxy-17-(3-methoxypropionyloxy)-6α-methyl-4-pregnene-3,20-dione, a compound of claim 1.

23. 11β,21-dihydroxy-17-methoxyacetoxy-6α-methyl-1,4-pregnadiene-3,20-dione, a compound of claim 1.

24. A pharmaceutical composition comprising an antiinflammatorily effective amount of a compound of claim 1 and a pharmaceutically acceptable carrier.

25. A pharmaceutical composition of claim 24 wherein the carrier is adapted for topical administration.

26. A pharmaceutical composition of claim 24 comprising 1 or 2 antiinflammatory agents.

27. A method of treating inflammation in a patient in need of such treatment comprising administering an amount of a compound of claim 1 effective for such treatment.

* * * * *